US010796037B1

(12) United States Patent
Trias

(10) Patent No.: US 10,796,037 B1
(45) Date of Patent: Oct. 6, 2020

(54) PADE-WEIERSTRASS ANALYTIC CONTINUATION TECHNIQUE FOR THE EFFICIENT ENFORCEMENT OF CONTROL LIMITS IN POWER-FLOW STUDIES

(71) Applicant: Antonio Trias, Sant Cugat del Valles (ES)

(72) Inventor: Antonio Trias, Sant Cugat del Valles (ES)

(*) Notice: Subject to any disclaimer, the term of this patent is extended or adjusted under 35 U.S.C. 154(b) by 11 days.

(21) Appl. No.: 15/838,099

(22) Filed: Dec. 11, 2017

Related U.S. Application Data

(60) Provisional application No. 62/434,452, filed on Dec. 15, 2016.

(51) Int. Cl.
*G06F 30/20* (2020.01)
*G06F 17/12* (2006.01)
*G06F 111/10* (2020.01)

(52) U.S. Cl.
CPC ............. *G06F 30/20* (2020.01); *G06F 17/12* (2013.01); *G06F 2111/10* (2020.01)

(58) Field of Classification Search
None
See application file for complete search history.

(56) References Cited

U.S. PATENT DOCUMENTS

2011/0257933 A1* 10/2011 Trias ...................... G01R 21/00
702/182
2014/0156094 A1* 6/2014 Trias ...................... G06F 30/367
700/291

OTHER PUBLICATIONS

Subramanian, M. K. (2014). Application of holomorphic embedding to the power-flow problem (Doctoral dissertation, Arizona State University) (Year: 2014).*

* cited by examiner

Primary Examiner — Bijan Mapar

(57) ABSTRACT

A system and method is presented for efficiently enforcing control limits in the calculation of powerflow studies of electrical power systems, using the Holomorphic Embedding Load-flow Method. The method applies to any automatic control in which the controlling resource is limited by a maximum or minimum value, such as Mvar limits in generators, the tap ratio in load-changing transformers, or real power output in AGC-participating generators. One key element of this invention consists in devising an equality constraint, holomorphically embedded, able to encode the switching behavior between the different control modes when limit thresholds are reached. The other key element is a novel analytic continuation scheme, here referred to as "Padé-Weierstrass", which achieves the continuation to $s=1$ by means of several intermediate steps of power series re-expansions on the path from $s=0$ to $s=1$ in embedding parameter space. This technique exploits the great numerical stability of Padé approximants, which in the particular case of the power-flow problem have guaranteed convergence properties granted by Stahl's theorem. The Padé-Weierstrass technique provides the level of precision and numerical stability that is needed to perform the analytic continuation up to $s=1$ under the new equality constraint. The result is a greatly improved computational efficiency in the calculation of large powerflow studies in which control limits need to be enforced.

12 Claims, 4 Drawing Sheets

PADE-WEIERSTRASS ANALYTIC CONTINUATION TECHNIQUE FOR THE EFFICIENT ENFORCEMENT OF CONTROL LIMITS IN POWER-FLOW STUDIES

CROSS REFERENCE TO RELATED APPLICATIONS

The present application claims the benefit of U.S. Patent Application Ser. No. 62/434,452 entitled "A PADE-WEIERSTRASS ANALYTIC CONTINUATION TECHNIQUE FOR THE EFFICIENT ENFORCEMENT OF CONTROL LIMITS IN POWER-FLOW STUDIES", filed on Dec. 15, 2016, the entire teachings of which are incorporated herein by reference.

GOVERNMENT LICENSE RIGHTS

This invention was made with government support under contract no. NNX15CC10C awarded by the National Aeronautics and Space Administration. The government has certain rights in the invention.

BACKGROUND

Systems and methods herein generally relate to the problem of calculating powerflow studies of electrical networks, and more particularly to methods for incorporating and enforcing the physical limits of system controls in those studies, which is essential for the faithful simulation of power systems in their steady-state.

Powerflow studies need to incorporate the effects of several kinds of automatic regulating devices that are always present in the operation of electrical networks. In what follows, they will be generically referred to as controls. A non-exhaustive list of the most interesting ones, from the point of view of steady-state powerflows, comprises: voltage regulation by generators (AVR, Automatic Voltage Regulation) or by transformers (ULTC, Under-Load Tap Changers), frequency regulation by generators participating in AGC (Automatic Generation Control), real power regulation by phase shifters, reactive power regulation by transformers, and net real power regulation across tie lines (area interchange schedules). Additionally, controls may be local or remote. Some remote controls may be real, enabled by modern fast telecommunications; others are just convenient artifacts used only in the context of planning studies (e.g. area interchange schedules). Whatever the case, a power flow method needs to incorporate all these types of control in order to be useful for real engineering work. One crucial aspect, which is the subject of the present invention, is the correct enforcement of control limits in power flow calculations. For instance, automatic voltage regulation in a generator is limited by the minimum and maximum values of reactive power output (which in turn are determined by the limits in the rotor exciter current and other heating effects); when those limits are reached, the control resource "saturates" and can no longer sustain the desired voltage setpoint.

Traditional iterative powerflows deal with controls using either one of these two general approaches: (a) incorporating additional equations and new control variables into the definition of the matrix of the method (possibly eliminating some variables if they are given directly by the control setpoints); (b) keeping the original equations and using an "outer loop" approach, whereby the control variables are adjusted in between iterations, in proportion to the residuals of the regulated magnitude. The proportionality coefficients for these adjustments, the so-called sensitivities, are obtained either by theoretical modeling, direct computation, or empirical tests. This option (b) is favored by methods that keep the Jacobian constant through the iterations, such as the FDLF (Fast Decoupled Load Flow) method of Stott and Alsac (B. Stott, "Review of load-flow calculation methods", *Proceedings of the IEEE*, vol. 62, no. 7, pp. 916-929, 1974), because it allows taking into account control limits in a fast manner. This, however, makes convergence behavior even harder to model and analyze. By contrast, the treatment of limits in method (a) requires a change in the equations in between iterations (for instance, a PV to PQ bus-type switch), so it would be more suited for a full NR (Newton Raphson) method (Stott 1974, ibid.).

Enforcing control limits raises several challenges in powerflow studies. The main one is that it makes the solution harder to arrive at. Iterative methods generally will take more iterations to converge, and, moreover, subtle interactions between controls (due to the nonlinear nature of the problem) may, unfortunately, produce "oscillations", in which one or more controls should be bounced off from their limits from one iteration to the next, therefore preventing convergence. Over the years, many heuristic techniques have been devised to improve the convergence rate of the industry-standard Newton-Raphson and Fast Decoupled powerflows in the presence of limits, with varying degrees of success. To date, it is a fair assessment to say that this problem has not been fully solved, as it keeps appearing in the everyday work of powerflow practitioners.

Additionally, most efforts have been devoted only to improving the chances of convergence, accelerating the convergence rate, and avoiding oscillations between saturated and non-saturated states. In contrast, very little has been done to address the problem of choosing among the possibly different configurations of saturated and non-saturated control states that may be valid. In other words, since the problem may have multiple non-equivalent solutions due to nonlinearities, some sort of criteria is needed in order to select one. The trouble with both iterative approaches (a) and (b) mentioned above is that this issue is not even contemplated: the decisions as to which controls should or should not reach saturation are just the result of the unpredictable "dynamics" of the numerical iteration. The result is that the inherent problems of fractality in iterative methods (which may cause either divergence or landing on a low-voltage solution, unpredictably) are then compounded by this somewhat arbitrary choice of saturated controls, dictated purely by numerical iteration.

Note that in cases in which there exists any additional information to help decide the relative priorities for saturation, such information may be trivially incorporated by powerflow methods. For instance, information about the timing response of controls; or about the operational details of their mutual coordination may be arbitrarily included. But, the invention disclosed here is concerned with the general scenario in steady-state powerflow studies, where none of this information is available and, consequently, this selection problem remains unsolved.

In contrast with iterative powerflow methods, U.S. Pat. Nos. 7,519,506 and 7,979,239, to Trias, take a very different approach to controls. The method, from here onwards termed the Holomorphic Embedding Load-flow Method (HELM), is non-iterative, constructive, and takes advantage of the specific mathematical structure of the power flow problem by using the techniques of Complex Analysis. Before the invention disclosed here, HELM dealt with controls by using a two-layered approach: a first layer incorporated control equations considering unlimited controlling resources, therefore using equality constraints for the setpoints. The smooth properties of these equality constraints allow them to be holomorphically embedded, thus preserving all the nice deterministic properties of the core HELM method. A second layer then took care of control limits by adding the inequality constraints for the control resources. However, this second problem was solved as an optimization problem, out of the core HELM methodology. In fact, that "outer loop" approach allowed the method to be used with any other powerflow methods in order to deal with control limits. By contrast, the invention disclosed here consists in solving the problem of control limits completely within the framework of HELM.

Seemingly related methods come from the area known as "Optimal Power Flow" (OPF). However, the problem of OPF is quite different from the standard steady-state powerflow one. Many of the magnitudes that in a powerflow study are given as fixed parameters become free variables in OPF, subject to global optimization under some prescribed functional and possibly additional constraints. Even so, as mentioned above, the enforcement of control limits may cause a power-flow problem to have multiple possible valid solutions, and therefore the selection problem may also be tackled via OPF techniques. However, this involves minimization, which has a very high computational cost and does not have guarantees of convergence, since this optimization problem cannot be proven to be convex in general.

SUMMARY

The present disclosure is framed under the general field of powerflow studies (also known as load-flow studies) of power systems. The method disclosed herein comprises a procedure for contemplating and correctly enforcing the effect of limits of control devices (also known as regulating devices) in the calculation of the operating steady-state solution of electrical power networks, using the Holomorphic Embedding Load-flow Method (HELM). The method disclosed herein contemplates any general type of control device for which the controlling resource (such as injected Mvar, MW, a tap ratio, or any other physical resource) has physical hard limits that must be observed and enforced in the powerflow solution.

All controls in a power network are subject to physical limits, either in their controlling resource or in some output magnitude. When such limits are reached, the control mode switches to a different, limited behavior. The enforcement of control limits then raises two different kinds of challenges in powerflow studies. The first one is that it makes the solution harder to arrive at: iterative methods converge at a slower rate, and, moreover, control saturations may exhibit oscillatory behavior between iterations. The second kind of challenge is seldom recognized, but quite fundamental: for feasible powerflows, there may be more than one acceptable solution, the only difference among them being the particular choice of control devices saturated at their physical limits.

The innovation disclosed here addresses the two aforementioned problems. It is based on an extension of HELM that allows the incorporation of these limiting effects under the methods of the holomorphic embedding technique in a seamless way. It therefore achieves the calculation of the desired solution by a direct construction, it avoids non-operational solutions, and solves the problem of limit-induced multiplicity of operational solutions by letting analytic continuation automatically select the configuration that is connected to the unambiguous reference state at $s=0$. Additionally, just as the base HELM method, it correctly signals when the problem is infeasible.

This extension of HELM consists in the following two main advances: (1) a new way to encode the switching between the several different behaviors (i.e., control modes) of the control devices as an equality constraint, instead of several disconnected regimes separated among themselves by inequality constraints; (2) a new technique to perform the analytic continuation of the holomorphically embedded voltages, substantially more numerically stable than the direct one-step analytic continuation performed in the base HELM method. It is found that the numerical stability provided by (2) is absolutely needed in order to solve the new problem posed by (1), which introduces singularities near the embedding end point, $s=1$.

The behavior of controls can be typically characterized by considering separate behavior regions, also known as control modes. Generically, one may consider at least a normal operating mode, in which the control resource is able to satisfy the commanded setpoint; and saturated modes, in which either the control resource or a target magnitude hits a limit (upper or lower), and the control tries to prevent violations of the limit. Separately, each mode is conductive to a mathematical expression readily amenable for inclusion in powerflow calculations—they become algebraic equality constraints added to the system. But the difficulty lies in dealing with all modes together at the same time, using a mathematically smooth formulation, which is why most methods resort to "bus-type switching" (in other words, explicitly alternating between control modes in the calculation). In the invention herein disclosed, all modes of a given control are combined multiplicatively into a single equality constraint, and adequately embedded so that the system must definitely obey one of the possible modes at the embedding limit, $s=1$.

The equality constraint solves the problem of bringing the multiple control modes under a holomorphic treatment, but it introduces a singularity right at the end point of the embedding, $s=1$, precisely because the constraint expresses a bifurcation of choices at that point (the system must obey one of the control modes at that point). It is found that the standard HELM procedure for evaluating the voltage functions at $s=1$, which is based on a single-step analytic continuation achieved via Padé approximants, is clearly insufficient because of the numerical instabilities associated with these newly introduced singularities. By Stahl's theorem (H. Stahl, "The convergence of Padé approximants to functions with branch points", J. of Approximation Theory, vol. 91, pp. 139-204, 1997), it is known that the Padé approximants will converge very slowly when approaching such branching points.

This last problem is solved by performing the analytic continuation in several intermediate steps along a path on the real axis from $s=0$ to $s=1$, instead of just one. This is in the spirit of the classical Weierstrass path analytic continuation (J. E. Marsden and M. J. Hoffman, "Basic Complex Analysis", W. H. Freeman, 1988), but with the addition of a key inventive approach that exploits the specific nature of the power-flow problem, and in particular the HELM technique. The approach consists in re-writing the power-flow equations at any generic intermediate point $s_0^{(k)}$ between 0 and 1, making use of the voltages $V(s_0^{(k)})$ at that point in the embedding procedure. By Stahl's theorem, these values can always be obtained very accurately thanks to the properties of Padé approximants, as long as singularities are not too close. Then the key point is that one is able to re-parameterize the re-written equations in such a way that one recovers formally the same HELM equations as before. Applying this procedure repeatedly, one is able to approach the point s=1 with significantly enhanced numerical stability, because the successive re-parameterizations act as a sort of zooming device that always keeps the target point s=1 sufficiently away, for the purposes of HELM evaluation.

DETAILED DESCRIPTION

The power flow equations that describe the steady-state of a basic power system, comprised of constant PQ power injections plus (optionally) constant current injection terms, are given by the current balance at each bus, as follows:

$$\sum_{j=0}^{n} Y_{ij}^{(tr)} V_j + Y_i^{(sh)} V_i = I_i + \frac{S_i^*}{V_i^*} \quad (1)$$

Figure 1:
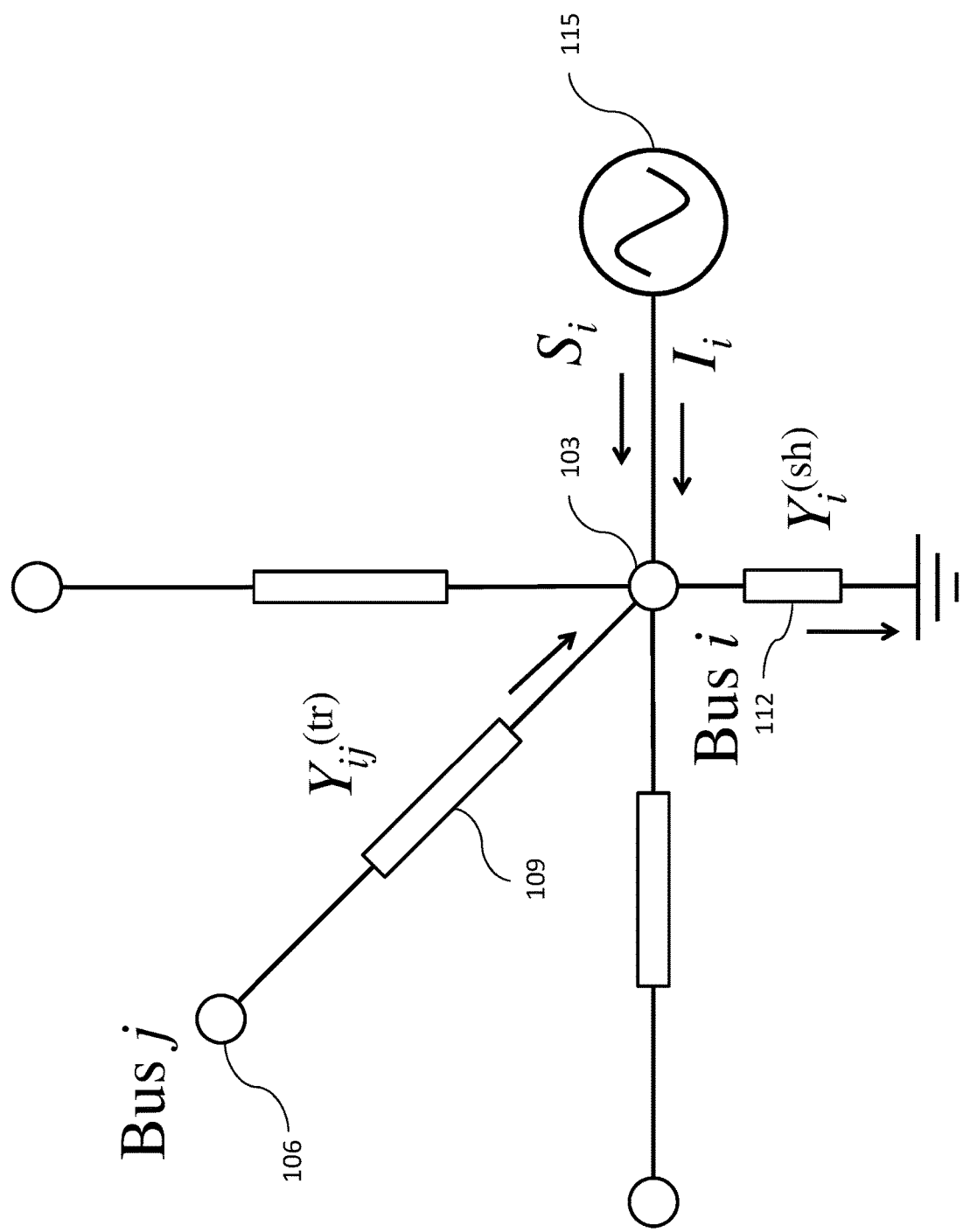
FIG. 1 is a schematic representation of a power network, displaying the sign conventions for voltage and power flow magnitudes as they are used in the description of the systems and methods herein disclosed.

FIG. 1 depicts the nomenclature and sign conventions used in the description of the systems and methods herein disclosed. This schematic drawing illustrates a generic bus in an electric power network. Equation (1) holds for the voltage $V_i$ at each bus i 103, and the summation on the right hand side runs over all neighbor buses j 106, which are linked by transmission lines 109 having admittances $-Y_{ij}^{(tr)}$ 109. The diagonal of the admittance matrix, $Y_{ii}^{(tr)}$, is the sum of the admittances of all branches (lines and transformers) incident on bus i. The shunt term $Y_i^{(sh)}$ 112 is meant to include both the line charging susceptance and any other constant-impedance modeling component of the load or any other device attached to the bus. Each bus i 103 may also have constant current $I_i$ or constant power injections $S_i$ provided by a load or generator 115. Constant-current injections can always be dropped from the mathematical treatment because they can be eliminated by linear transformations and the resulting equations take on the same form, albeit with transformed parameters. Without loss of generality, a swing bus is assumed at index 0. In each equation, the sum goes over all bus indices, including the swing bus. There is one equation per non-swing bus, labeled by index i.

On the other hand, there exist several types of control devices on the network, designed to regulate voltage, VARs flow, or other magnitudes. From the point of view of steady-state powerflows, controls are additional equality constraints on the problem. In turn, each constraint necessarily introduces a corresponding controlling variable, also known as the controlling resource, in order to keep the number of equations and the number of degrees of freedom (i.e., the actual number of free variables) balanced. For instance, the prime and most ubiquitous example is the automatic voltage regulation (AVR) at so-called PV buses, where the controlling resource is the reactive injection Q provided by the attached generator. Other examples of control resources are the tap ratio a in regulating transformers (so-called ULTC transformers), or the number of steps in switched shunt capacitor banks. Adding automatic controls to the powerflow problem would still result in smooth algebraic equations, if it were not for the existence of hard limits: control resources are always limited. For instance, generators VARs (Q injection) have lower and upper physical limits; ULTC transformer taps have minimum and maximum settings; and automatically switched shunts are limited by the number of capacitors in the bank. These limits add new inequality constraints to the equations, and this is what causes the sort of problems mentioned in the Background section.

The embodiment herein disclosed exemplifies the treatment of the most important control device, namely the automatic voltage control (AVR) at generator buses. The treatment of other control devices follows the same principles, and can be developed by a person having ordinary skill in the art.

Disregarding control limits momentarily, voltage regulation at generator buses modifies the original system of equation (1) by adding a set of equality constraints on the voltages: the voltage modulus of the bus must be equal to the regulation setpoint. Correspondingly, an equal number of parameters are now freed as variables, in order to balance the number of equations and unknowns. In this case, the new free variables are the reactive power injections $Q_p$ at generator buses. This splits the system into two sets of equations, one for load buses (also called PQ-type buses) and one for generator buses (also called PV-type buses), plus the addition of the constraint equations:

$$\sum_{j=0}^{n} Y_{ij}^{(tr)} V_j + Y_i^{(sh)} V_i = \frac{S_i^*}{V_i^*}, \quad i \in \{PQ\} \quad (2)$$

$$\sum_{j=0}^{n} Y_{pj}^{(tr)} V_j + Y_p^{(sh)} V_p = \frac{P_p}{V_p^*} - j\frac{Q_p}{V_p^*}, \quad p \in \{PV\}$$

$$|V_p| = V_p^{(sp)}, \quad p \in \{PV\}$$

However, the variables $Q_p$, are limited by the maximum and minimum Mvar output limits of the generator, $Q_p^{(min)}$ and $Q_p^{(max)}$. When either limit is reached, the control mode switches its behavior: it regulates $Q_p$ at the limiting value, and the voltage is allowed to depart from the setpoint. This last behavior is therefore equivalent to that of a PQ-type bus. To accommodate this bus-type switching behavior under the holomorphic embedding technique, a suitable embedding must be devised.

The standard HELM embedding for the system with equation (2), in the absence of control limits, is as follows:

$$\sum_{j=0}^{n} Y_{ij}^{(tr)} V_j(s) = -sY_i^{(sh)} V_i(s) + s\frac{S_i^*}{V_i^*(s^*)}, \quad i \in \{PQ\} \quad (3)$$

$$\sum_{j=0}^{n} Y_{pj}^{(tr)} V_j(s) + j\frac{Q_p(s)}{V_p^*(s^*)} = -sY_p^{(sh)} V_p(s) + s\frac{P_p}{V_p^*(s^*)}, \quad p \in \{PV\}$$

$$V_p(s)V_p^*(s^*) = 1 + s\left((V_p^{(sp)})^2 - 1\right), \quad p \in \{PV\}$$

Here, the swing bus voltage is assumed to be normalized to 1. Alternatively, one may always embed the swing voltage trivially as $V_0=1+s(V_0^{(ref)}-1)$. Defining the shorthand notation $W_p=V_p V_p^*$, the equality constraints can be rewritten as:

$$W_p(s) - W_p^{(sp)} = (1-s)(1-W_p^{(sp)}) \quad (4)$$

The expressions for the limits on the control resources $Q_p$ constitute additional inequality constraints. To encode these together with the above equality constraints into one single constraint equation for each bus, the following expression is devised, which replaces equation (4):

$$(W_p(s)-W_p^{(sp)})(Q_p^{(max)}-Q_p(s))(Q_p(s)-Q_p^{(min)}) = -(1-s)(1-W_p^{(sp)})Q_p^{(max)}Q_p^{(min)} \quad (5)$$

The multiplicative form of this embedding guarantees that when s=1 the system will obey either of the control modes at each PV bus. At the same time, the constants are suitably chosen so that the embedding allows for satisfying the general guidelines of the HELM method regarding the reference solution at s=0, i.e., the solution where there are no injections and no flows across the system. This is readily verified because the constraint clearly admits the choice $V_p(0)=1$ and $Q_p(0)=0$ for all PV nodes p; this is the so-called 'white germ' of the HELM method. Therefore, at the end of the procedure, the power-flow solution attained at s=1 will contain a set of type-switched states that is the emergent result from the analytic continuation of this 'white germ.'

Next, the HELM procedure requires expressing all equations (including the constraint equation) in terms of the power series of all functions involved. One should arrive at a full-rank linear system that allows solving for all power series coefficients, order after order, in a sequential manner. Following the standard procedure in HELM, the equations for PQ nodes yield the following equation for the power series coefficients, at order N+1:

$$\sum_{j=0}^{n} Y_{ij}^{(tr)} V_j[N+1] = -Y_i^{(sh)} V_i[N] + S_i^* V_i^{-1*}[N] \quad (6)$$

Here $V_i^{-1*}[N]$ represents the power series coefficients of the function $1/V^*(s^*)$, which can be obtained from those of $V(s)$ simply by using the relationship $V(s) \cdot (1/V(s))=1$. On the other hand, the equation for PV nodes yield the following:

$$\sum_{j=0}^{n} Y_{pj}^{(tr)} V_j[N+1] + jQ_p[N+1] = -j \sum_{k=0}^{N-1} V_p^{-1*}[k+1]Q_p[N-k] - Y_p^{(sh)} V_p[N] + P_p V_p^{-1*}[N] \quad (7)$$

In this equation, the expressions resulting from the quotient $Q_p(s)/V_p^*(s)$ make use of the fact that $V_p^{-1}[0]=1$, and $Q_p[0]=0$. Then, as in the equation for PQ nodes, all coefficients that are already known from stage N are moved to the right hand side, and the true unknown variables are moved to the left.

The equations resulting from the constraints are more convoluted. To further simplify the notation, it is convenient to divide both sides of equation (5) by the product $Q_p^{(min)} Q_p^{(max)}$, and defining $\mu_p = (Q_p^{(min)}+Q_p^{(max)})/(Q_p^{(min)} Q_p^{(max)})$ and $q_p^2(s) = Q_p^2(s)/(Q_p^{(min)} Q_p^{(max)})$, the constraint is rewritten as:

$$(W_p(s)-W_p^{(sp)})(1-\mu_p Q_p(s)+q_p^2(s)) = (1-s)(1-W_p^{(sp)}) \quad (8)$$

Using the power series representation for all the functions involved in this expression, one arrives at the following equation for the coefficients at order N+1:

$$W_p[N+1] - \mu_p(1-W_p^{(sp)})Q_p[N+1] = \quad (9)$$
$$(W_p^{(sp)}-1)\delta_{N,0} + \mu_p \sum_{k=0}^{N-1} W_p[k+1]Q_p[N-k] - $$
$$\sum_{k=0}^{N-1} W_p[k+1]q_i^2[N-k] - (1-W_p^{(sp)})q_p^2[N+1]$$

Here $\delta$ is the Kronecker delta. Note again how some of the convolutions have been simplified using the fact that $W_p[0]=1$ and $Q_p[0]=0$. Additionally, the term $q_p^2[N+1]$ has been moved to the right hand side because, since $q_p^2(s)=Q_p^2(s)/(Q_p^{(min)} Q_p^{(max)})$ and $Q_p[0]=0$, it can be easily shown that it suffices to know all coefficients of $Q_p(s)$ up to order N in order to calculate the (N+1)-th coefficient of $q_p^2(s)$. As for the coefficients of $W_p(s)=V_p(s)V_p^*(s^*)$, they can be obtained from those of $V_p(s)$:

$$W_p[N+1] = \quad (10)$$
$$\sum_{k=0}^{N+1} V_p[N+1-k]V_p^*[k] = 2\mathrm{Re}V_p[N+1] + \sum_{k=1}^{N} V_p[N+1-k]V_p^*[k]$$

The equation for the constraint finally becomes:

$$2\mathrm{Re}V_p[N+1] - \mu_p(1-W_p^{(sp)})Q_p[N+1] = (W_p^{(sp)}-1)\delta_{N,0} - \quad (11)$$
$$\sum_{k=1}^{N} V_p[N+1-k]V_p^*[k] + \mu_p \sum_{k=0}^{N-1} W_p[k+1]Q_p[N-k] - $$
$$\sum_{k=0}^{N-1} W_p[k+1]q_i^2[N-k] - (1-W_p^{(sp)})q_p^2[N+1]$$

Therefore equations (6), (7), and (11) form a well-defined, full-rank linear system where the variables are all the voltage coefficients $V_i[N+1]$ (at both PQ and PV buses) plus the injections $Q_p[N+1]$ at PV buses. Given that equation (11) involves the real part of $V_p[N+1]$, this linear system can be made more manageable by writing it in terms of the real and imaginary parts of the voltages. This last rearrangement, and the solution of the system by means of linear algebra techniques (exploiting the sparsity of the admittance matrix) is straightforward to any person having ordinary skill in the art, and therefore will not be detailed here. By obtaining all these coefficients at order N+1, it becomes possible to compute the new right-hand-side terms for preparing the next linear system, at order N+2. By solving these linear systems sequentially, it is thus possible to construct the power series of all functions involved in the problem, arbitrarily to any order, within the limits of memory, computational time, and finite precision of floating point arithmetic.

Having computed the power series, the last step of the HELM method consists in evaluating the voltages at s=1 by means of analytic continuation. By virtue of Stahl's theorem, near-diagonal Padé approximants provide this directly.

Moreover, since Stahl proved that the approximants converge on the maximal domain of analytic continuation, they provide a reliable test of feasibility: if the Padé approximants converge at s=1, the value is the operating solution (defined as the one analytically continued from the reference 'white germ'); if the Padé approximants oscillate at s=1, the problem is infeasible. However, the new constraint equation (5) introduces a significant practical problem. By design, each constraint generates a branching point precisely at s=1, each branch corresponding to one of the three possible control modes. This causes the point s=1 to always sit right at the border between convergence and non-convergence of the Padé approximants. As expected, one verifies experimentally that this convergence does indeed become exceedingly slow near s=1, making the scheme impractical.

At this point, the second key inventive technique of the method is disclosed. Padé approximants show very slow convergence if one tries to reach the point s=1, but Stahl's theorem still guarantees that their convergence will be fast for values sufficiently away from the branch points and branch cuts of the function. This can provide us with very precise values of $V(s_0)$, at some intermediate value $0<s_0<1$. On the other hand, analytic continuation can be performed in several steps, following a path in s-space, in the spirit of Weierstrass original ideas. However, a straightforward implementation of the Weierstrass procedure, i.e., re-evaluation of the power series at each point along the path, is, in general, numerically unstable, as shown by Henrici and other authors (P. Henrici, "An Algorithm for Analytic Continuation", SIAM Journal on Numerical Analysis, Vol. 3, No. 1, pp. 67-78, 1966). Here the key approach consists in exploiting the particular nature of the power-flow equations and Stahl's theorem in order to perform path analytic continuation in a numerically stable manner, as developed below. The technique will therefore be referred to as "Padé-Weierstrass".

The following procedure will show how to use the partial solution obtained at a value $0<s_0<1$, together with an adequate re-parameterization, in order to obtain a derived HELM power flow problem that is formally the same as the original one (except for the particular values of some parameters, which are easy to re-compute). This allows one to progressively approach the point s=1 by solving a succession of HELM problems, each of them numerically stable. It will now be shown how these HELM power flow problems adopt the following common form:

$$\sum_{j=0}^{n} Y_{ij}^{(tr)} V_j(s) = -sY_i^{(sh)} V_i(s) + \frac{sS_i^*}{V_i^*(s^*)} + \Gamma_i\left(\frac{1}{V_i^*(s^*)} - V_i(s)\right) \quad (12)$$

$$\sum_{j=0}^{n} Y_{pj}^{(tr)} V_j(s) + j\frac{Q_p(s)}{V_p^*(s^*)} =$$

$$-sY_p^{(sh)} V_p(s) + \frac{sP_p}{V_p^*(s^*)} + \Gamma_p\left(\frac{1}{V_p^*(s^*)} - V_p(s)\right)$$

$$(W_p(s) - W_p^{(sp)})(Q_p^{(max)} - Q_p(s))(Q_p(s) - Q_p^{(min)}) =$$

$$-(1-s)(1-W_p^{(sp)})Q_p^{(max)}Q_p^{(min)}$$

As before, the index i is used to label PQ buses, and index p is used to label PV buses. These equations are formally the same as the original power-flow problem, except for the new injections parameterized by $\Gamma_i$. This is no obstacle, as one can set $\Gamma=0$ on the first Padé Weierstrass step. However, it will be shown how these terms become non-null in subsequent steps.

By Stahl's theorem, there will always be a value $0<s_0<1$ such that the near-diagonal Padé approximants converge to the analytic continuation of the reference germ with very good precision. Note that $s_0$ does not necessarily have to be chosen real, and therefore many other complex-valued paths from 0 to 1 could also be valid, in principle. However, for simplicity of the implementation, the values $s_0$ will be here restricted to be real-valued (additionally, physical considerations dictate that the reference solution should always be analytic-continuable along the real axis, up to the first encounter with a point of voltage collapse). A simple bisection strategy can then be used in order to find the highest value of $s_0$ such that the voltages $V_i(s_0)$ achieve the desired precision. Evaluating equation (12) on these values, and multiplying the first two expressions respectively by $V_i^*(s_0)$ and $V_p^*(s_0)$, one obtains the following relationships, which will be used later:

$$\sum_{j=0}^{n} V_i^*(s_0) Y_{ij}^{(tr)} V_j(s_0) = -s_0 Y_i^{(sh)} |V_i(s_0)|^2 + s_0 S_i^* + \Gamma_i(1 - |V_i(s_0)|^2) \quad (13)$$

$$\sum_{j=0}^{n} V_p^*(s_0) Y_{pj}^{(tr)} V_j(s_0) + jQ_p(s_0) =$$

$$-s_0 Y_p^{(sh)} |V_p(s_0)|^2 + s_0 P_p + \Gamma_p(1 - |V_p(s_0)|^2)$$

$$(W_p(s_0) - W_p^{(sp)})(Q_p^{(max)} - Q_p(s_0))(Q_p(s_0) - Q_p^{(min)}) =$$

$$-(1-s_0)(1-W_p^{(sp)})Q_p^{(max)}Q_p^{(min)}$$

The following re-parameterization of the embedding variable is now defined:

$$s = s_0 + (1-s_0)s' \quad (14)$$

At the same time, the following change of variables will be used:

$$V_j'(s') = \frac{V_j(s)}{V_j(s_0)} \quad (15)$$

$$Q_p'(s') = Q_p(s) - Q_p(s_0)$$

In the new parameter s', the point s'=0 corresponds to the point $s=s_0$, at which a partial solution has been calculated. The point s'=1 corresponds to the point s=1, the target end point. On the other hand, the change of variables is designed so that the new reference solution at s'=0 is again the canonical 'white germ' of the HELM method, i.e., voltages equal to 1 everywhere and injections equal to zero everywhere.

Beginning with the equations for PQ nodes, the change of variables yields the following equation, after multiplying both sides by $V_i^*(s_0)$:

$$\sum_{j=0}^{n} V_i^*(s_0) Y_{ij}^{(tr)} V_j(s_0) V_j'(s') = \quad (16)$$

$$-sY_i^{(sh)} |V_i(s_0)|^2 V_i'(s') + \frac{sS_i^*}{V_i'^*(s'^*)} + \Gamma_i\left(\frac{1}{V_i'^*(s'^*)} - |V_i(s_0)|^2 V_i'(s')\right)$$

It is now useful to introduce the shorthand notation:

$$\hat{Y}_{ij} \equiv V_i^*(s_0) Y_{ij}^{(tr)} V_j(s_0) \tag{17}$$

However, unlike the original matrix $Y_{ij}^{(tr)}$, this new admittance matrix does not satisfy the transmission condition (i.e., the sum of all columns does not yield the zero column vector). In fact, the sum of its columns can be readily calculated using equation (13) above:

$$\sum_{j=0}^{n} \hat{Y}_{ij} = -s_0 Y_i^{(sh)} |V_i(s_0)|^2 + s_0 S_i^* + \Gamma_i (1 - |V_i(s_0)|^2), \; i \in \{PQ\} \tag{18}$$

$$\sum_{j=0}^{n} \hat{Y}_{pj} = -jQ_p(s_0) - s_0 Y_p^{(sh)} |V_p(s_0)|^2 + s_0 P_p + \Gamma_p (1 - |V_p(s_0)|^2),$$

$$p \in \{PV\}$$

This should be fixed by defining the new admittance matrix as follows:

$$Y_{ij}^{\prime(tr)} \equiv \begin{cases} \hat{Y}_{ij} & i \neq j \\ \hat{Y}_{ii} - \sum_{j=0}^{n} \hat{Y}_{ij} & i = j \end{cases} \tag{19}$$

With these definitions and after straightforward algebraic rearrangements and simplifications of equation (16), one arrives at the following equation for PQ nodes:

$$\sum_{j=0}^{n} Y_{ij}^{\prime(tr)} V_j'(s') = -s' Y_i^{\prime(sh)} V_i'(s') + \frac{s S_i^{\prime *}}{V_i^{\prime *}(s^{\prime *})} + \Gamma_i' \left( \frac{1}{V_i^{\prime *}(s^{\prime *})} - V_i'(s') \right) \tag{20}$$

Comparing this with equation (12), it is verified that the problem takes on exactly the same form, except that the admittance matrix and all other parameters change values (although the sparsity pattern of the admittance matrix remains the same, which can be exploited for computational performance). The new parameters in this expression are found to be as follows:

$$\hat{Y}_i^{(sh)} \equiv (1-s_0)|V_i(s_0)|^2 Y_i^{(sh)}$$

$$S_i' \equiv (1-s_0) S_i$$

$$\Gamma_i' \equiv \Gamma_i + s_0 S_i^* \tag{21}$$

The corresponding equation for PV nodes is obtained by carrying out completely analogous calculations:

$$\sum_{j=0}^{n} Y_{pj}^{\prime(tr)} V_j'(s') + j \frac{Q_p'(s')}{V_p^{\prime *}(s^{\prime *})} =$$

$$-s' Y_p^{\prime(sh)} V_p'(s') + \frac{s' P_p'}{V_p^{\prime *}(s^{\prime *})} + \Gamma_p' \left( \frac{1}{V_p^{\prime *}(s^{\prime *})} - V_p'(s') \right) \tag{22}$$

In this case the parameters are:

$$\hat{Y}_i^{(sh)} \equiv (1-s_0) |V_i(s_0)|^2 Y_i^{(sh)}$$

$$P_i' \equiv (1-s_0) P_i \tag{23}$$

$$\Gamma_i' \equiv \Gamma_i + s_0 P_i - j Q_p(s_0)$$

Comparing this result with the original equation (12), it is verified again that it is formally the same, but with different parameters. It remains to verify that the constraint equation can also be brought into the same form as in equation (12). The following definitions will be used now:

$$W_p'(s') \equiv V_p'(s') V_p^{\prime *}(s^{\prime *}) = \frac{V_p(s)}{V_p(s_0)} \frac{V_p^*(s^*)}{V_p^*(s_0)} = \frac{W_p(s)}{W_p(s_0)} \tag{24}$$

$$W_p^{\prime(sp)} \equiv (V_p^{\prime(sp)})^2 \equiv \frac{(V_p^{(sp)})^2}{|V_p(s_0)|^2} = \frac{W_p^{(sp)}}{W_p(s_0)}$$

$$Q_p^{\prime(min)} \equiv Q_p^{(min)} - Q_p(s_0)$$

$$Q_p^{\prime(max)} \equiv Q_p^{(max)} - Q_p(s_0)$$

Making use of the constraint relationship evaluated at the partial solution $V_p(s_0)$ (third expression in equation (13) above), one arrives at the expression for the constraint in the new variables and the embedding parameter s':

$$(W_p'(s) - W_p^{\prime(sp)})(Q_p^{\prime(max)} - Q_p'(s'))(Q_p'(s) - Q_p^{\prime(min)}) = -(1-s')(1-W_p^{\prime(sp)}) Q_p^{\prime(max)} Q_p^{\prime(min)} \tag{25}$$

This completes the verification that the Padé-Weierstrass procedure does generate a new HELM power flow problem that is formally identical to the original one.

The procedure can be repeated several times, thus providing a method to approach the critical point s=1 by solving a sequence of numerically stable HELM power flow problems. Labeling each Padé-Weierstrass stage with an index k, and assuming that the whole procedure is stopped at a step $k_{end}$ such that the proximity to s=1 is within the required numerical tolerance, the final solution is easily obtained from the values of all partial solutions:

$$V_j = V_j^{(1)}(s_0^{(1)}) \cdot V_j^{(2)}(s_0^{(2)}) \cdot V_j^{(3)}(s_0^{(3)}) \ldots V_j^{(kend)}(s_0^{(kend)})$$

$$Q_p = Q_p^{(1)}(s_0^{(1)}) + Q_p^{(2)}(S_0^{(2)}) + Q_p^{(3)}(s_0^{(3)}) + \ldots Q_p^{(k_{end})}) \tag{26}$$

Figure 2A:
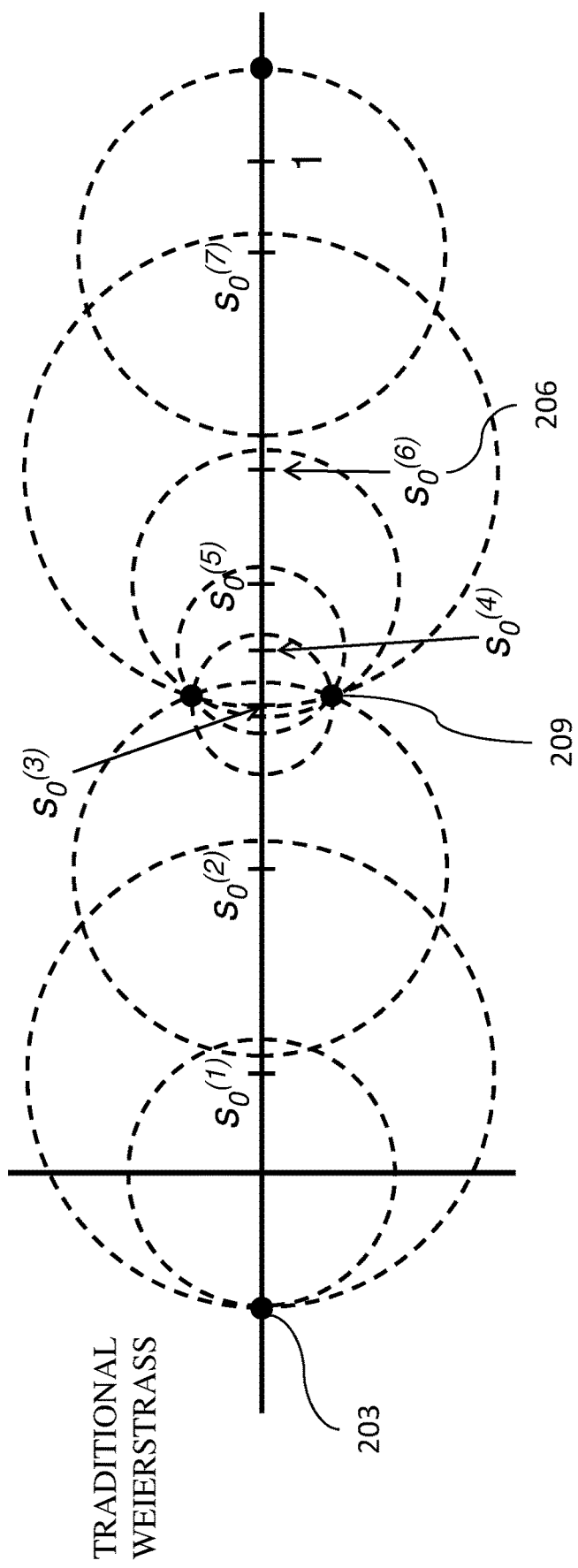
FIG. 2A is a diagram illustrating the process of analytic continuation using a standard Weierstrass procedure.
Figure 2B:
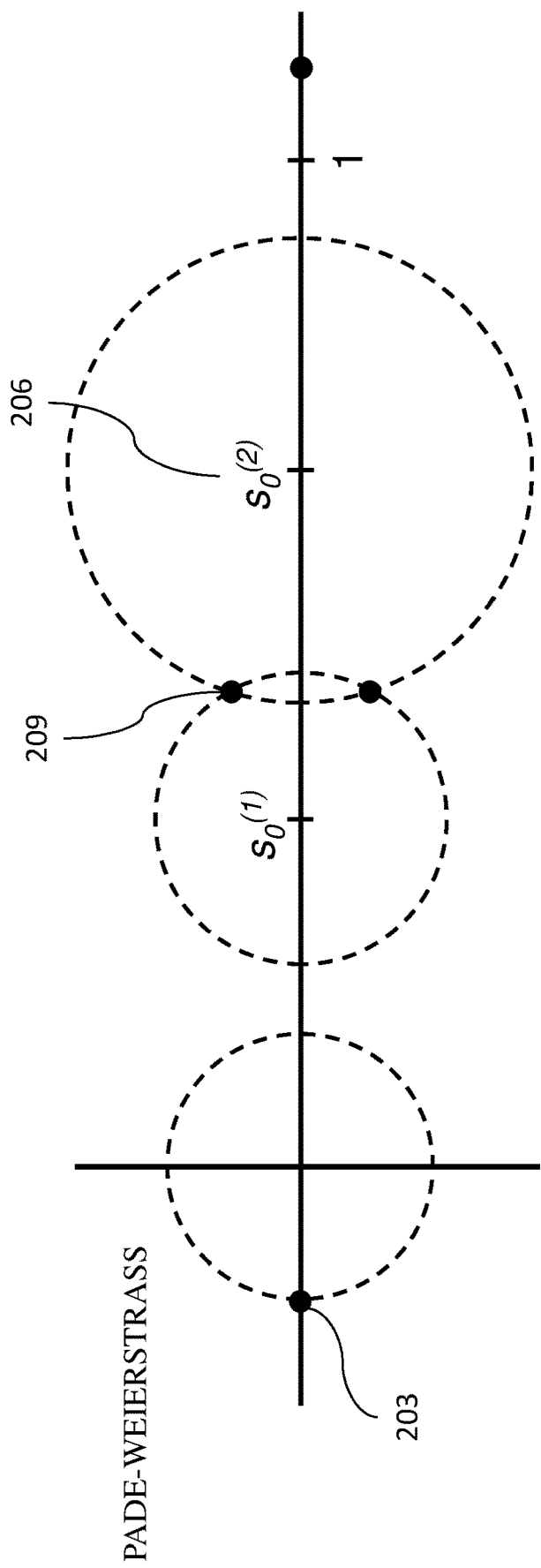
FIG. 2B is a diagram illustrating the process of analytic continuation using a Padé-Weierstrass technique.

FIGS. 2A and 2B are graphical comparisons of the Padé-Weierstrass procedure, disclosed herein, versus a traditional Weierstrass path analytic continuation. When attempting traditional (i.e., power series-based) Weierstrass analytic continuation along the real axis towards the point s=1, the radius of convergence of each power series sets the limit for the maximum distance that can be traveled to the new point on which the next power series will be based. In the example shown in FIG. 2A, the initial power series, based around the point s=0, has a radius of convergence set by the nearest singularity point 203, which limits the next point $s_0^{(1)}$ to be within this distance to 0. The newly obtained power series will have a new radius of convergence, given by the closest singularity to the new center point $s_0^{(1)}$. The procedure continues analogously for successive points 206 $s_0^{(2)}$, $s_0^{(3)}$, $s_0^{(4)}$, etc. The existence of complex singularities 209 on the s-plane anywhere near the real segment (0,1) may therefore hinder the procedure severely, as it would force the calculation of many steps, as seen in FIG. 2A. This problem is compounded by the numerical instability inherent in the direct construction of a new power series from the original power series, which renders the procedure useless for most practical problems. By contrast, as seen in FIG. 2B, the Padé-Weierstrass procedure disclosed herein exploits the properties of near-diagonal Padé approximants conferred by Stahl's theorem, together with some nice properties of the embedded power-flow equations under reparameterization.

At each intermediate stage of the procedure, Padé approximants can provide the function values (not the power series) at points $s_0^{(k)}$ far outside the radius of convergence of the power series, with great precision. Combining this with the reparameterization technique described above, and solving the resulting HELM power flow problem, one obtains a new power series based around the evaluation point $s_0^{(k)}$. The number of analytic continuation steps needed is therefore much lower, and, what is more important, each one retains high accuracy due to the numerical stability of Padé approximants on all the intermediate evaluation points.

Figure 3:
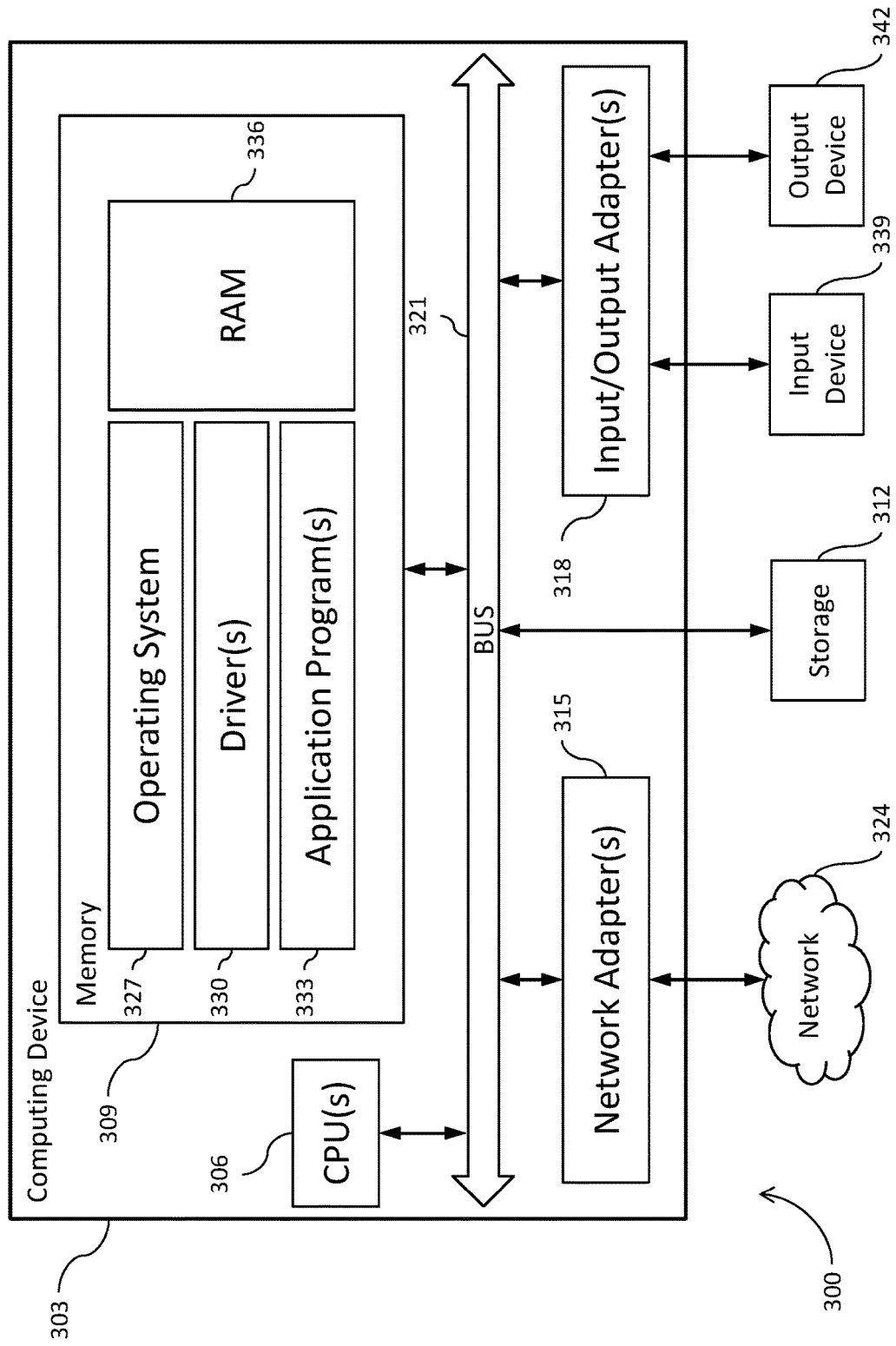
FIG. 3 is a schematic diagram of a hardware system according to systems and methods herein.

A representative hardware environment for practicing the systems and methods described herein is depicted in FIG. 3. This schematic drawing illustrates a hardware configuration of an information handling/computing system 300 in accordance with systems and methods herein. The computing system 300 comprises a computing device 303 having at least one processor or central processing unit (CPU) 306, internal memory 309, storage 312, one or more network adapters 315, and one or more input/output adapters 318. A system bus 321 connects the CPU 306 to various devices such as the internal memory 309, which may comprise random access memory (RAM) and/or read-only memory (ROM), the storage 312, which may comprise magnetic disk drives, optical disk drives, a tape drive, etc., the one or more network adapters 315, and the one or more input/output adapters 318. Various structures and/or buffers (not shown) may reside in the internal memory 309 or may be located in a storage unit separate from the internal memory 309.

The one or more network adapters 315 may include a network interface card such as a LAN card, a modem, or the like to connect the system bus 321 to a network 324, such as the Internet. The network 324 may comprise a data processing network. The one or more network adapters 315 perform communication processing via the network 324.

The internal memory 309 stores an appropriate Operating System 327, and may include one or more drivers 330 (e.g., storage drivers or network drivers). The internal memory 309 may also store one or more application programs 333 and include a section of Random Access Memory (RAM) 336. The Operating System 327 controls transmitting and retrieving packets from remote computing devices (e.g., host computers, storage systems, SCADA, etc.) over the network 324. In some systems and methods, a Supervisory and Data Acquisition Systems and/or Energy Management Systems may connect to the computing system 300 over the network 324. The drivers 330 execute in the internal memory 309 and may include specific commands for the network adapter 315 to communicate over the network 324. Each network adapter 315 or driver 330 may implement logic to process packets, such as a transport protocol layer to process the content of messages included in the packets that are wrapped in a transport layer, such as Transmission Control Protocol (TCP) and/or Internet Protocol (IP).

The storage 312 may comprise an internal storage device or an attached or network accessible storage device. Storage 312 may include disk units and tape drives, or other program storage devices that are readable by the system. A removable medium, such as a magnetic disk, an optical disk, a magneto-optical disk, a semiconductor memory, or the like, may be installed on the storage 312, as necessary, so that a computer program read therefrom may be installed into the internal memory 309, as necessary. Programs in the storage 312 may be loaded into the internal memory 309 and executed by the CPU 306. The Operating System 327 can read the instructions on the program storage devices and follow these instructions to execute the methodology herein.

The input/output adapter 318 can connect to peripheral devices, such as input device 739 to provide user input to the CPU 306. The input device 339 may include a keyboard, mouse, pen-stylus, microphone, touch sensitive display screen, or any other suitable user interface mechanism to gather user input. An output device 342 can also be connected to the input/output adapter 318, and is capable of rendering information transferred from the CPU 306, or other component. The output device 342 may include a display monitor (such as a Cathode Ray Tube (CRT), a Liquid Crystal Display (LCD), or the like), printer, speaker, etc.

The computing system 300 may comprise any suitable computing device 303, such as a mainframe, server, personal computer, workstation, laptop, handheld computer, telephony device, network appliance, virtualization device, storage controller, etc. Any suitable CPU 306 and Operating System 327 may be used. Application Programs 333 and data in the internal memory 309 may be swapped into storage 312 as part of memory management operations.

It is expected that any person skilled in the art can implement the disclosed procedure using a computer program. The computer program may include instructions that would be provided to a processor of a general purpose computer, special purpose computer, or other programmable data processing apparatus to produce a machine, such that the instructions that execute via the processor of the computer or other programmable data processing apparatus obtain powerflow solutions that observe and enforce control limits for a given network model under various realizations of the load, generation, and other parameters. The generalization of the example charts shown above to any other minimization procedure should be evident to any person skilled in the art.

As will be appreciated by one skilled in the art, aspects of the systems and methods herein may be embodied as a system, method, or computer program product. Accordingly, aspects of the present disclosure may take the form of an entirely hardware system, an entirely software system (including firmware, resident software, micro-code, etc.) or an system combining software and hardware aspects that may all generally be referred to herein as a "circuit," "module", or "system." Furthermore, aspects of the present disclosure may take the form of a computer program product embodied in one or more computer readable medium(s) having computer readable program code embodied thereon.

Any combination of one or more computer readable non-transitory medium(s) may be utilized. The non-transitory computer storage medium stores instructions, and a processor executes the instructions to perform the methods described herein. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a Read-Only Memory (ROM), an Erasable Programmable Read-Only Memory (EPROM or Flash memory), an optical fiber, a magnetic storage device, a portable compact disc Read-Only Memory (CD-ROM), an optical storage device, a "plug-and-play" memory device, like a USB flash drive, or any suitable combination of the foregoing. In the context of this document, a computer readable storage medium may be any tangible medium that can contain, or store a program for use by or in connection with an instruction execution system, apparatus, or device.

Program code embodied on a computer readable medium may be transmitted using any appropriate medium, including, but not limited to, wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Smalltalk, C++, or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The flowchart and block diagrams in the Figures illustrate the architecture, functionality, and operation of possible implementations of systems, methods, and computer program products according to various systems and methods herein. In this regard, each block in the flowchart or block diagrams may represent a module, segment, or portion of code, which comprises one or more executable instructions for implementing the specified logical function(s). It should also be noted that, in some alternative implementations, the functions noted in the block might occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular systems and methods only and is not intended to be limiting of this disclosure. As used herein, the singular forms "a", "an", and "the" are intended to include the plural forms as well, unless the context clearly indicates otherwise. It will be further understood that the terms "comprises", "comprising", "includes", and/or "including", when used in this specification, specify the presence of stated features, integers, steps, operations, elements, and/or components, but do not preclude the presence or addition of one or more other features, integers, steps, operations, elements, components, and/or groups thereof.

In addition, terms such as "right", "left", "vertical", "horizontal", "top", "bottom", "upper", "lower", "under", "below", "underlying", "over", "overlying", "parallel", "perpendicular", etc., used herein are understood to be relative locations as they are oriented and illustrated in the drawings (unless otherwise indicated). Terms such as "touching", "on", "in direct contact", "abutting", "directly adjacent to", etc., mean that at least one element physically contacts another element (without other elements separating the described elements).

The concepts herein have been described with references to specific systems and methods. While particular values, relationships, materials and steps have been set forth for purposes of describing such concepts, it will be appreciated by persons skilled in the art that numerous variations and/or modifications may be made to the systems and methods as shown in the disclosure without departing from the spirit or scope of the basic concepts and operating principles as broadly described. It should be recognized that, in the light of the above teachings, those skilled in the art could modify those specifics without departing from the concepts taught herein. Having now fully set forth certain systems and methods, and modifications of the concepts underlying them, various other systems and methods, as well as potential variations and modifications of the systems and methods shown and described herein, will obviously occur to those skilled in the art upon becoming familiar with such underlying concept. It is intended to include all such modifications and alternatives insofar as they come within the scope of the appended claims or equivalents thereof. It should be understood, therefore, that the concepts disclosed might be practiced otherwise than as specifically set forth herein. Consequently, the present systems and methods are to be considered in all respects as illustrative and not restrictive.

The invention claimed is:

1. A method, comprising:
generating a mathematical model of power flow equations for an electrical grid having load (PQ) buses and generator (PV) buses, the PQ buses and PV buses including control devices;
expressing the power flow equations in terms of power series of the functions involved;
embedding the mathematical model of the powerflow equations representing the electrical grid in a holomorphic embedding, the holomorphic embedding having a set of equality constraints for the electrical grid defining a linear system where variables of the powerflow equations are the coefficients at both PQ and PV buses;
transcribing the holomorphic embedding into software for use in a computer processor adapted to execute the software;
using the computer processor to compute an n-order algebraic approximant by means of Padé-Weierstrass approximants;
using the computer processor to evaluate the n-order algebraic approximant for the power series as a solution to the powerflow equations; and
displaying the solution to the powerflow equations as a measure of control of the electrical grid.

2. The method of claim 1, further comprising:
prior to holomorphically embedding the powerflow equations, receiving data from a supervisory and data acquisition system representative of conditions of the electrical grid associated with the powerflow equations.

3. The method of claim 2, further comprising:
forming the powerflow equations from the data received from the supervisory and data acquisition system.

4. The method of claim 1, further comprising:
solving the powerflow equations for the electrical grid using a load flow equation solver of the computer processor.

5. The method of claim 1, wherein the Padé-Weierstrass approximants use diagonal sequences of approximants in the Padé table.

6. The method of claim 1, further comprising:
determining values of the voltages in the powerflow equations by using all power coefficients obtained up to order N to construct the Padé-Weierstrass approximants.

7. The method of claim 6, further comprising:
repeating the procedure for the next order in N until desired accuracy is met.

8. A system comprising:
a power generating system having an electrical grid, wherein the electrical grid includes load (PQ) buses and generator (PV) buses, the PQ buses and PV buses including control devices;
a supervisory control and data acquisition system adapted to collect data from the electrical grid indicative of electrical conditions in the electrical grid; and
a computer processor adapted to execute software comprising executable computer instructions to:
generate a mathematical model of power flow equations for the electrical grid;
process data received from the supervisory control and data acquisition system into powerflow equations representing the electrical grid using the mathematical model;
express the power flow equations in terms of power series of the functions involved;
embed the mathematical model of the powerflow equations representing the electrical grid in a holomorphic embedding, the holomorphic embedding having a set of equality constraints for the electrical grid defining a linear system where variables of the powerflow equations are the coefficients at both PQ and PV buses;
compute an n-order algebraic approximant by means of Padé-Weierstrass approximants;
evaluate the n-order algebraic approximant for the power series as a solution to the powerflow equations; and
display the solution to the powerflow equations as a measure of control of the electrical grid.

9. The system of claim 8, wherein the computer processor further comprises a load flow equation solver solving the powerflow equations.

10. The system of claim 8, wherein the Padé-Weierstrass approximants use diagonal sequences of approximants in the Padé table.

11. The system of claim 8, wherein values of the voltages in the powerflow equations are determined by using all power coefficients obtained up to order N to construct the Padé-Weierstrass approximants.

12. The system of claim 8, wherein the computer processor repeats the procedure for the next order in N until desired accuracy is met.

* * * * *